United States Patent
Horgan et al.

(10) Patent No.: US 9,695,331 B2
(45) Date of Patent: Jul. 4, 2017

(54) SILICON-CONTAINING (METH) ACRYLATE COMPOUNDS

(71) Applicant: Arkema France, Colombes (FR)

(72) Inventors: James P. Horgan, West Chester, PA (US); Jeffrey A. Klang, West Chester, PA (US); Yuhong He, Honey Brook, PA (US); James Goodrich, Exton, PA (US)

(73) Assignee: Arkema France, Colombes (FR)

( * ) Notice: Subject to any disclaimer, the term of this patent is extended or adjusted under 35 U.S.C. 154(b) by 1092 days.

(21) Appl. No.: 13/859,100

(22) Filed: Apr. 9, 2013

(65) Prior Publication Data
US 2013/0266815 A1    Oct. 10, 2013

Related U.S. Application Data

(60) Provisional application No. 61/622,240, filed on Apr. 10, 2012.

(51) Int. Cl.
C07F 7/18        (2006.01)
C09D 133/14      (2006.01)
C08F 230/08      (2006.01)
C09D 143/04      (2006.01)

(52) U.S. Cl.
CPC .......... C09D 133/14 (2013.01); C07F 7/1836 (2013.01); C08F 230/08 (2013.01); C09D 143/04 (2013.01); C08L 2312/08 (2013.01); Y10T 428/31663 (2015.04)

(58) Field of Classification Search
CPC ............................... C07F 7/1836; C07C 57/02
See application file for complete search history.

(56) References Cited

U.S. PATENT DOCUMENTS

| | | | | |
|---|---|---|---|---|
| 5,233,006 | A * | 8/1993 | Wolter | C07F 7/182 |
| | | | | 526/279 |
| 5,352,816 | A | 10/1994 | Takeoka | |
| 5,696,179 | A | 12/1997 | Chawla | |
| 5,717,125 | A | 2/1998 | Wolter et al. | |
| 6,124,491 | A | 9/2000 | Wolter et al. | |
| 6,391,463 | B1 | 5/2002 | Fan et al. | |
| 6,933,401 | B2 * | 8/2005 | Molock | C07C 67/26 |
| | | | | 556/437 |

FOREIGN PATENT DOCUMENTS

| | | | | |
|---|---|---|---|---|
| CA | 2521629 A1 * | 11/2004 | ............ | C07F 7/1836 |
| EP | 2112189 A1 * | 10/2009 | ............ | C08F 230/08 |
| JP | 3552324 B2 | 8/2004 | | |
| JP | 2010229054 A * | 10/2010 | | |
| JP | 5034241 B2 | 9/2012 | | |
| WO | WO 96/12749 | 5/1996 | | |
| WO | WO 02097003 A1 * | 12/2002 | ............ | C08K 5/07 |

OTHER PUBLICATIONS

Machine Translation of JP 2010-229054 A, Sep. 2016.*
Translation of WO 02/97003 A1, Sep. 2016.*
Wolter et al., "Multifunctional (Meth)Acrylate AlkoxySilane: A New Type of Reactive Compounds", MRS Proceedings, vol. 271, 1992, pp. 719-724.*
PCT/EP2013/057393 (Search Report), Apr. 9, 2013, Arkema France.
"A Simple Method for the Reinforcement of UV-Cured Coatings via Sol-Gel Photopolymerization"—Macromolecular Material and Engennering pp. 506-516; C. Belon, A. Chemtob, C. Croutxe-Barghorn, S. Rigolet, V. Houerou, C. Gauthier.
"Combination of Radical and Cationic Photoprocesses for the Single-Step Synthesis of Organic-Inorganic Hybrid Films"—Journal of Polymer Science vol. 48 pp. 4150-4158 C. Belon, A. Chemtob, C. Croutxe-Barghorn, S. Rigolet, V. Le Houerou, C. Gauthier.
"Silane Coupling Agents Improve Performance" Modern Paint and Coatings Feb. 1996 pp. 34-39; Bruce A. Waldman OSI Specialties Inc.

* cited by examiner

*Primary Examiner* — Nicole M Buie-Hatcher
(74) *Attorney, Agent, or Firm* — Christopher R. Lewis

(57) ABSTRACT

The present invention includes silicon-containing (meth) acrylate compounds of formula (I):

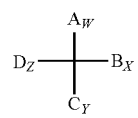

(I)

where A is a $C_1$-$C_{12}$ organic moiety such as an alkyl or aryl moiety, B is a silane functional group, C is a (meth)acrylate functional group and D is an allyl functional group, with w=0 or 1, z=0, 1 or 2, x=1, 2 or 3, y=1, 2 or 3 and w+x+y+z=4. The compounds are suitable for use in curable compositions, such as peroxide-curable compositions or radiation-curable compositions and may be applied to a substrate as a coating or sealant, for example. Compositions containing the silicon-containing (meth)acrylate compounds may have reduced volatility and odor problems along with improved adhesion to substrates, increased crosslink density and/or improved hardness.

17 Claims, No Drawings

SILICON-CONTAINING (METH) ACRYLATE COMPOUNDS

CROSS REFERENCE TO RELATED APPLICATIONS

This application claims benefit to U.S. application No. 61/622,240, filed on Apr. 10, 2012, which is hereby incorporated by reference in its entirety.

FIELD OF THE INVENTION

The invention relates to silicon-containing (meth)acrylate compounds which may be useful as coupling agents or adhesion promoters in free radical curable compositions, such as UV curable and peroxide curable coatings, for example. The compounds may also be useful as resins in hybrid free radical/cationic cure UV curable coatings or 2-part cure coating systems using peroxides and acid initiators, for example. Additionally, the compounds may be useful as coupling agents in peroxide cured elastomer and composite resin systems as well as in peroxide cured concrete sealant and bulk cure systems.

BACKGROUND OF THE INVENTION

Radiation curing has become more and more a technology of choice for several reasons. Radiation curing provides low or zero emission of volatile organic compounds (VOCs), is energy efficient, does not require combustion of fossil fuels, which produces resultant carbon dioxide emissions and provides high productivity. Radiation cure technology is widely used in coatings, inks and adhesives. The curable compositions may include mixtures of monomers, oligomers, photoinitiators and additives which are applied to a substrate and cured in place via exposure to ultraviolet (UV) light. The adhesion of the cured compositions to substrates varies from system to system. Various additives have been used to improve adhesion. For example, silane agents have been widely used to improve adhesion in traditional coatings and composites based on epoxy chemistry. However, the application and selection of silane agents depends on cure mechanisms. In the case of radiation curable compositions, only one compound, gamma-methacryloxypropyl trimethoxysilane, is compatible with the cure mechanism and is readily available. Other silane-based coupling agents are available, but are mainly directed to two-part, non-(meth)acrylate systems. See Waldman, Silane Coupling Agents Improve Performance, Modern Paints and Coatings, February, 1996.

Gamma-methacryloxypropyl trimethoxysilane monomer is a commercially available coupling agent for bonding coatings to substrates. The coupling agent may be mixed with other copolymerizable monomers, such as (meth)acrylates (e.g., acrylates, methacrylates or mixtures thereof) and the mixture of monomers may be applied to a surface and cured. The methacryloxypropyl trimethoxysilane coupling agent of the prior art is prepared from allyl methacrylate, a volatile, odorous compound which is also a strong skin and eye irritant. The presence of the allyl methacrylate starting material along with the methacryloxypropyl trimethoxysilane monomer coupling agent also causes odor problems with the cured coatings.

The methacryloxypropyl trimethoxysilane coupling agent of the prior art is also a mono-methacrylate and is extractible from coatings when not fully polymerized and crosslinked into the cured network. In certain applications, this extractible monomer may be considered as an undesirable contaminant. The adhesion benefits obtained from this monomer are also limited because it only contains a single trimethoxy group to promote adhesion or coupling to substrate or fillers.

U.S. Pat. No. 6,391,463 is directed to alkoxylated modification of a methacryloxypropyl trimethoxysilane coupling agent as a means to overcome odor and skin and eye irritancy. It is also based on an easier to handle alkoxylated allyl methacrylate precursor. This improvement is limited, however, as the disclosed compositions still only contain a single methacrylate function and a single trimethoxysilane adhesion promoting functional group. Additionally, the composition is based on alkoxylate allyl methacrylate, which is not commercially available.

WO 96/12749 is directed to silane oligomers and radiation curable coating compositions for optical fiber coating. The silane oligomers are high in molecular weight (e.g., 500-11,000) and a high level of silane oligomer is needed, typically about 5-99% of the coating composition. These silane oligomers are typically prepared based on urethane chemistry and urethane linkage.

The abstract for DE-4416857 relates to hydrolysable and polymerizable silanes, which have carboxylic acid functional groups, for use in free radical polymerization. The silane agents are prepared from hydroxy containing compounds and acid anhydride containing silanes.

Additionally, there is developing art where curable silanes may be used with other cure technologies to make harder, more durable "nanocomposite" type coatings and adhesives. For example, university researchers are investigating reinforcement of UV cured coatings by incorporating alkoxy silane/(meth)acrylate functional components in formulas with both free radical and cationic generating photoinitiators thereby causing formation of sol-gel networks within acrylic polymer networks on exposure to UV irradiation. See Journal of Polymer Science, Part A, Polymer Chemistry, Vol 48, 4150-4158 (2010) and Macromolecular Materials and Engineering, 2011, vol. 296, issue 6, pp. 506-516.

There remains a need, however, for cure technologies having reduced volatility and odor while still providing effective adhesion performance, hardness, etc.

SUMMARY OF THE INVENTION

The present invention includes silicon-containing meth (acrylate) compounds, methods of making the same and curable compositions comprising the same. The silicon-containing (meth)acrylate compounds may be useful as coupling agents, adhesion promoters and resins in coatings and sealants, for example.

The invention provides for polymerizable coupling agents having reduced volatility and odor. The polymerizable coupling agents may match or exceed the adhesion performance of the coupling agents already available, but avoid the volatility and odor problems. The coupling agents also provide tunable functionality for free radical or cationic crosslinking in addition to adhesion promotion properties.

Improved UV free radical, UV hybrid free radical/cationic, peroxide and 2-part peroxide/cationic curable coating and sealant compositions may be obtained, which have reduced volatility and odor, improved adhesion to substrates, increased crosslink density, reduced extractibles and improved hardness, for example. Improved properties in peroxide cured rubber, elastomer and composite compositions may also be obtained, for example, by incorporating fillers and reinforcers, such as carbon black, glass fiber, synthetic fiber and silaceous materials.

In one embodiment of the present invention, the silicon-containing (meth) acrylate compounds which further bear allylic groups.

Another embodiment relates to curable compositions comprising at least one of said (meth)acrylate compounds and also to the resulting cured compositions.

The invention further is directed to a polymer or copolymer resulting from the polymerization or copolymerization of at least one of the (meth)acrylate compounds of the invention and also a related coated substrate as a substrate coated by said curable composition.

The invention further relates to related reinforced compositions of rubber, elastomer or composite.

A specific precursor compound suitable for preparing the said compounds is also part of the invention as is a process of preparation of said (meth)acrylate compounds by reacting a silane specific compound with an allyl(meth)acrylate compound.

Another aspect of the present invention relates to silicon-containing (meth)acrylates.

In one embodiment of the present invention, the silicon-containing meth(acrylate) compound comprises, consists essentially of, consists of, is a compound or a mixture of compounds of formula (I) where:

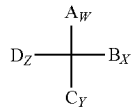

(I)

A is a $C_1$-$C_{12}$ organic moiety, such as an alkyl or aryl moiety,

B is a silane functional group with formula —$CH_2O(R_2)_m$ $(CH_2)_3SiX_3$ where X=a halogen, $C_1$-$C_6$ alkyl, $C_1$-$C_6$ alkoxy or aromatic radical, C is a (meth)acrylate functional group with formula —$CH_2O(R_2)_m$ (C=O)C($R_1$)=$CH_2$ where $R_1$ is H or $CH_3$ and D is an allyl functional group with formula —$CH_2O(R_2)_m$ $CH_2C(H)=CH_2$, where w=0 or 1, x=1, 2 or 3, y=1, 2 or 3 and z=0, 1, or 2 and w+x+y+z=4, where $R_2$ for each functional group is the same or different and is an oxyalkylene or polyoxyalkylene unit comprised of n repeating units of oxyalkylene such as oxyethylene [$CH_2CH_2O$] or oxypropylene [$CH_2CH(CH_3)$ O], with mixture of said oxyalkylene units being also possible, a caprolactone or polycaprolactone unit, comprised of n repeating units of formula —[C(=O)($CH_2$)$_5$O]— or a lactide or polylactide unit, comprised of n repeating units of formula —[C(=O)CH($CH_3$)O]—, n is an integer with a value from 1 to 12 and m is 0 or 1.

Mixtures of different compounds in accordance with formula (I) are also contemplated by the present invention.

The silicon-containing meth(acrylate) compound or compounds may be used in curable compositions, such as peroxide-curable or radiation-curable compositions. The radiation-curable compositions may include free radical-curable, cationic-curable or dual-curable free radical and cationic hybrid curable compositions.

In another embodiment of the present invention, a compound of formula (III) is provided which is useful or suitable as an intermediate or as a precursor, in the preparation of compounds according to formula (I), particularly by reacting said precursor with a silane compound of formula (II) H—Si (X)$_3$, with X being a halogen, a $C_1$-$C_6$ alkyl, $C_1$-$C_6$ alkoxy or an aromatic radical.

Said precursor compound is of formula (III) as defined below:

(III)

where:

A is a $C_1$-$C_{12}$ organic moiety such as an alkyl or aryl moiety,

C is a (meth)acrylate functional group with formula $CH_2O(R_2)_m$(C=O)C($R_1$)=$CH_2$ where $R_1$ is H or $CH_3$, D is an allyl functional group with formula —$CH_2O(R_2)_m$ $CH_2C(H)=CH_2$, and w=0 or 1, y=1, 2 or 3 and z=1, 2 or 3 and w+y+z=4, where $R_2$ for each functional group is the same or different and is an oxyalkylene or polyoxyalkylene unit comprised of n repeating units of oxyalkylene such as oxyethylene [$CH_2CH_2O$] or oxypropylene [$CH_2CH(CH_3)O$], a caprolactone or polycaprolactone unit, comprised of n repeating units of formula —[C(=O)($CH_2$)$_5$O]— or a lactide or polylactide unit, comprised of n repeating units of formula —[C(=O)CH($CH_3$)O], n being an integer with a value from 1 to 12 and m is 0 or 1.

This same precursor compound may also be depicted as a compound of formula (I) according to the formula I:

(I)

wherein:

A is a $C_1$-$C_{12}$ organic moiety, such as an alkyl or aryl moiety

B is a silane functional group with formula $CH_2O(R_2)_m$ $(CH_2)_3SiX_3$ where X=a halogen, a $C_1$-$C_6$ alkyl, a $C_1$-$C_6$ alkoxy or an aromatic radical, C is a (meth)acrylate functional group with formula $CH_2O(R_2)_m$(C=O)C($R_1$)=$CH_2$ where $R_1$ is H or $CH_3$, D is an allyl functional group with formula $CH_2O(R_2)_m$ $CH_2C(H)=CH_2$, and w=0 or 1, x=0, y=1, 2 or 3, and z=1, 2 or 3 and w+x+y+z=4, $R_2$ for each functional group is the same or different and is an oxyalkylene or polyoxyalkylene unit comprised of n repeating units of oxyalkylene such as oxyethylene [$CH_2CH_2O$] or oxypropylene [$CH_2CH(CH_3)$ O], a caprolactone or polycaprolactone unit, comprised of n repeating units of formula —[C(=O)($CH_2$)$_5$O]— or a lactide or polylactide unit, comprised of n repeating units of formula —[C(=O)CH($CH_3$)O], n being an integer with a value from 1 to 12 and m is 0 or 1.

In another embodiment of the present invention, a method of making a compound of formula (I) comprises:

reacting a silane compound of formula (II)

H—Si(X)$_3$        (II)

on at least one allyl functional group of an allyl (meth) acrylate compound (precursor) of formula (III):

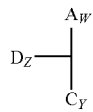
(III)

as defined above, in the presence of a transition metal catalyst.

DETAILED DESCRIPTION OF THE INVENTION

Aspects of the present invention include silicon-containing meth(acrylate) compounds, methods of making the same, curable compositions comprising the same and coupling agents, adhesion promoters, resins, coatings and sealants obtainable from the compositions.

A silicon-containing meth(acrylate) compound according to the present invention corresponds to formula (I)

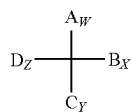
(I)

where A is an optional $C_1$-$C_{12}$ organic moiety such as alkyl or aryl, B is a silane functional group, C is a (meth)acrylate functional group and D is an optional allyl functional group.

As used herein and in the claims, the terms "comprising" and "including" are inclusive or open-ended and do not exclude additional unrecited elements, compositional components or method steps. Accordingly, the terms "comprising" and "including" encompass the more restrictive terms "consisting essentially of" and "consisting of". Unless specified otherwise, all values provided herein include up to and including the endpoints given and the values of the constituents or components of the compositions are expressed in weight percent or % by weight of each ingredient in the composition.

Each compound used herein may be discussed interchangeably with respect to its chemical formula, chemical name, abbreviation, etc. For example, MA may be used interchangeably with meth(acrylate) or a compound that has either an acrylate ($CH_2$=CHCOO—) or a methacrylate ($CH_2$=CMeCOO—) group, where Me is a methyl group. Additionally, any polymer described herein, unless designated otherwise, includes homopolymers, copolymers, terpolymers and the like.

The silicon-containing meth(acrylate) compound of the invention corresponds to formula (I)

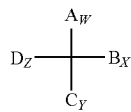
(I)

$A_w$ is a $C_1$-$C_{12}$ organic moiety, such as alkyl, aryl or other organic moiety, where w is 0 or 1 i.e., the compound may contain either no A organic moiety or a single A organic moiety. The alkyl group may include a functional group or side-chain that consists solely of single-bonded carbon and hydrogen atoms. For example, the alkyl groups may be straight chain, branched or cyclic and may be a group such as methyl, ethyl, propyl, butyl, pentyl, hexyl, heptyl, octyl, nonyl, decyl, undecyl, dodecyl and the like. The aryl group refers to any functional group or substituent derived from an aromatic ring, such as phenyl, naphthyl, thienyl, indolyl, etc. The other organic moieties encompass organic (carbon-based) moieties known to one of ordinary skill in the art, which would be suitable for use in the silicon-containing meth(acrylate) compounds of the present invention.

The alkyl group, aryl group or other organic moiety may be unsubstituted or substituted. An "unsubstituted" group refers to groups that do not contain heteroatoms and includes straight chain groups, branched chain isomers of straight chain groups, cyclic groups, such as cyclopropyl, cyclobutyl, cyclopentyl, cyclohexyl, cycloheptyl and cyclooctyl and such rings substituted with straight and branched chain groups as defined above and may include primary, secondary or tertiary groups.

A "substituted" group refers to an unsubstituted group as defined above in which one or more bonds to carbon(s) or hydrogen(s) are replaced by a bond to non-hydrogen and non-carbon atoms including, but not limited to, a halogen atom, such as F, Cl, Br and I; an oxygen atom in groups such as hydroxyl groups, alkoxy groups, aryloxy groups and ester groups; a sulfur atom in groups such as thiol groups, alkyl and aryl sulfide groups, sulfone groups, sulfonyl groups and sulfoxide groups; a nitrogen atom in groups such as amines, amides, alkylamines, dialkylamines, arylamines, alkylarylamines, diarylamines, N-oxides, imides and enamines; a silicon atom in groups such as in trialkylsilyl groups, dialkylarylsilyl groups, alkyldiarylsilyl groups and triarylsilyl groups and other heteroatoms in various other groups. Substituted groups also include groups in which one or more bonds to carbon or hydrogen atoms are replaced by a bond to a heteroatom, such as oxygen in groups such as carbonyls, carboxyls and esters; nitrogen in groups such as imines, oximes, hydrazones and nitriles.

Each of the alkyl, aryl or other organic moiety may have, for example, 1 to 12 carbon atoms, 1 to 10 carbon atoms, 1 to 5 carbon atoms or 1 to 3 carbon atoms. In a preferred embodiment, A is a $C_2$ alkyl, namely, a $CH_2CH_3$ group where w is 1.

B is a silane functional group, which includes moieties containing at least one silicon-carbon bond. The value of x in formula (I) may be 1, 2 or 3 (i.e., the is compound may contain one, two or three B silane functional groups, where the silane functional groups may be the same as or different from each other when x is 2 or 3). In particular, B may have the formula —$CH_2O(R_2)_m(CH_2)_3SiX_3$ where X=a halogen, a $C_1$-$C_6$ alkyl, a $C_1$-$C_6$ alkoxy or an aromatic radical, where $R_2$ is an oxyalkylene or polyoxyalkylene unit, a caprolactone or polycaprolactone unit or a lactide or polylactide unit and m is 0 or 1.

With respect to X, the halogen atom may be any of the halogen elements listed in Group 17 of the periodic table, such as F, Cl, Br and I. The alkyl group may include any of the alkyl groups discussed above in detail for A. The alkoxy group includes alkyl groups where a carbon atom is bonded to at least one oxygen atom. Each of the alkyl or alkoxy groups may have, for example, 1 to 6 carbon atoms, 1 to 5 carbon atoms or 1 to 3 carbon atoms. In an exemplary embodiment, X is a $C_1$ or $C_2$ alkoxy (methoxy or ethoxy).

The aromatic radical may include, for example, homocyclics with the formula $C_nH_n$, where n is twice an odd number (e.g., benzene), heterocyclics where one or more of the atoms in the aromatic ring is of an element other than carbon, polycyclics containing two or more simple aromatic rings fused together by sharing two neighboring carbon atoms and substituted aromatics.

With respect to $R_2$, $R_2$ may include an oxyalkylene or polyoxyalkylene unit, a caprolactone or polycaprolactone unit or a lactide or polylactide unit. In particular, the oxyalkylene or polyoxyalkylene unit may include $[CH_2CH_2O]$, (e.g., polyoxyethylene) or $[CH_2CH(CH_3)O]_n$, (e.g., polyoxypropylene), the caprolactone or polycaprolactone unit may be of formula $[C(=O)(CH_2)_5O]_n$ or the lactide or polylactide unit may be of formula $[C(=O)CH(CH_3)O]_n$. n is an integer with a value from 1 to 12 or in particular from 1 to 5. In an exemplary embodiment, m equals 0 and $R_2$ is not present.

C is a (meth)acrylate functional group. The value of y in formula (I) may be 1, 2 or 3 (i.e., the compound may contain one, two or three (meth)acrylate functional groups per molecule, with these functional groups being the same as or different from each other when y is 2 or 3). The (meth)acrylate functional group may comprise two carbon atoms double bonded to each other and a carbonyl carbon (a carbon atom double-bonded to an oxygen atom). In particular, the (meth)acrylate functional group may comprise formula $-CH_2O(R_2)_m(C=O)C(R_1)=CH_2$ where $R_1$ is H or $CH_3$, $R_2$ is an oxyalkylene or polyoxyalkylene unit, a caprolactone or polycaprolactone unit or a lactide or polylactide unit as discussed for B, m is 0 or 1 and n is an integer with a value from 1 to 12 or in particular from 1 to 5. In an exemplary embodiment, m equals 0 and $R_2$ is not present.

D is an allyl functional group. The value of z in formula (I) may be 0, 1 or 2 (i.e., the compound may contain zero, one or two allyl functional groups per molecule, which may be the same as or different from each other where z is 2). Each allyl functional group may comprise a methylene ($-CH_2-$) group and a vinyl group ($-CH=CH_2$). In particular, the allyl functional group may comprise formula $-CH_2O(R_2)_mCH_2C(H)=CH_2$ where $R_2$ is an oxyalkylene or polyoxyalkylene unit, a caprolactone or polycaprolactone unit or a lactide or polylactide unit as discussed for B, m is 0 or 1 and n is an integer with a value from 1 to 12 or in particular from 1 to 5. In an exemplary embodiment, m equals 0 and $R_2$ is not present.

In formula (I), w=0 or 1, x=1, 2 or 3, y=1, 2 or 3 and z=0, 1 or 2 and the sum of w+x+y+z equals 4. The compound of the invention thus contains at least one (meth)acrylate functional group and at least one silane functional group per molecule and may optionally contain one or two allyl functional groups per molecule. In one embodiment, z=0 or 1, w=1 and A is a $C_1$ ($CH_3$) or $C_2$ alkyl ($CH_2CH_3$) group and $R_1$ is $CH_3$ or H, X is a methoxy or ethoxy and m=1 and n=1-5 where $R_2$ is an oxyalkylene or polyoxyalkylene unit. In another embodiment, z=0 or 1, w=0 and $R_1$ is $CH_3$ or H, X is a methoxy or ethoxy and m=1 and n=1-5 where $R_2$ is an oxyalkylene or polyoxyalkylene. According to another embodiment, z=0 or 1, w=1, A is a $C_1$ or $C_2$ alkyl group, $R_1$ is $CH_3$ or H, m=0 and X is methoxy or ethoxy. According to another embodiment z=0 or 1, w=0, $R_1$ is $CH_3$ or H, m=0 and X is methoxy or ethoxy.

According to a preferred embodiment of the monomer compound of the invention of formula (I), said $R_2$ radical is an oxyalkylene or polyoxyalkylene unit of formula $-[CH_2CH_2O]_n-$ or $-[CH_2CH(CH_3)O]_n-$, where n is an integer with a value from 1 to 12, in particular from 1 to 5.

The monomer compounds in accordance with formula (I) may be obtained from any suitable reactants known to one of ordinary skill in the art. In particular, monomer compounds in accordance with formula (I) may be obtained as the reaction products of at least one silane and of at least one allyl-containing (meth)acrylate, for example, in the presence of at least one transition metal catalyst.

Suitable allyl(meth)acrylates are trimethylol propane diallyl mono(meth)acrylate, trimethylol propane monoallyl di(meth)acrylate, triethylol propane diallyl mono(meth)acrylate, triethylol propane monoallyl di(meth)acrylate, pentaerythritol monoallyl tri(meth)acrylate, pentaerythritol diallyl di(meth)acrylate, pentaerythritol triallyl mono(meth)acrylate. These allyl(meth)acrylate compounds can be prepared by one skilled in the art by esterification using (meth)acrylic acid or by transesterification using methyl methacrylate of commercially available allyl products which are partial allyl ethers of polyols such as trimethylolpropane allyl ethers (mono- or di-allyl ethers) and pentaerythritol allyl ethers (mono-di- or tri-allyl ethers) which are commercially available from Perstorp.

Suitable silanes include, but are not limited to, halogenated silanes, alkoxylated silanes, alkyl silanes and aromatic silanes. Halogenated silanes may include silanes containing one or more halogen atoms, such as chlorine, bromine, fluorine, etc. For example, the halogenated silanes may include three or more halogen atoms, such as trichlorosilane, tribromosilane and trifluorosilane. Alkoxylated silanes may include silanes containing at least one oxygen and an alkyl group, such as methyl, ethyl, etc. For example, the alkoxylated silanes may include three or more oxygen atoms and three of more alkyl groups, such as trimethoxysilane and triethoxysilane. Alkyl silanes may include silanes containing one or more alkyl groups, such as methyl, ethyl, etc. For example, the alkyl silanes may include three or more alkyl groups, such as trimethylsilane. Aromatic silanes may include silanes containing at least one aromatic group. For example, the aromatic silanes may include three or more aromatic groups, such as triphenylsilane. In one embodiment, the silane of formula (II) is selected from the group consisting of trichlorosilane, tribromosilane, trifluorosilane, trimethoxysilane, triethoxysilane, trimethylsilane, triphenylsilane and mixtures thereof. The preferred silane may include an alkoxylated silane, such as trimethoxysilane or triethoxysilane, more preferably trimethoxysilane.

In one embodiment, the novel monomer compounds may be the addition (reaction) products in the presence of a transition metal catalyst of at least one silane compound of formula (II):

$$H-Si(X)_3 \tag{II}$$

on at least one allyl functional group of an allyl (meth)acrylate compound of formula (III) which allyl(meth)acrylate compound corresponds to the precursor compound of formula (III) as defined above according to the present invention with formula as follows

(III)

where:
A is a $C_1$-$C_{12}$ organic moiety as defined above for formula (I),
C is a (meth)acrylate functional group with formula —$CH_2O(R_2)_m(C$=$OC(R_1))$=$CH_2$ where $R_1$ is H or $CH_3$ as defined above for formula (I), and
D is an allyl functional group with formula —$CH_2O(R_2)_m CH_2C(H)$=$CH_2$ as defined above for formula (I),
where w=0 or 1, y=1, 2 or 3 and z=1, 2 or 3 and the sum of w+y+z=4. $R_2$ (if present, as m can be 0 or 1) is an oxyalkylene or polyoxyalkylene unit, such as $[CH_2CH_2O]_n$ or $[CH_2CH(CH_3)O]_n$, a caprolactone or polycaprolactone unit of formula $[C($=$O)(CH_2)_5O]_n$ or a lactide or polylactide unit of formula $[C($=$O)CH(CH_3)O]_n$, is an integer with a value from 1 to 12, in particular 1 to 5 and m is 0 or 1.

Suitable silanes of formula (II) where H—$Si(X)_3$ include, but are not limited to, silanes where X is a halogen, alkoxy, alkyl or aromatic, e.g., halogenated silanes, alkoxylated silanes, alkyl silanes and aromatic silanes. Halogenated silanes may include, for example, trichlorosilane, tribromosilane or trifluorosilane. Alkoxylated silanes may include, for example, trimethoxsilane or triethoxysilane. Alkyl silanes may include, for example, trimethylsilane. Aromatic silanes may include, for example, triphenylsilane. In one embodiment, the silane of formula (II) is selected from the group consisting of trichlorosilane, tribromosilane, trifluorosilane, trimethoxsilane, triethoxysilane, trimethylsilane, triphenylsilane and mixtures thereof. The preferred silane may include an alkoxylated silane, such as trimethoxysilane or triethoxysilane, more preferably trimethoxysilane.

Suitable allyl(meth)acrylates of formula (III) include, but are not limited to, trimethylol propane diallyl mono(meth)acrylate, trimethylol propane monoallyl di(meth)acrylate, triethylol propane diallyl mono(meth)acrylate, triethylol propane monoallyl di(meth)acrylate, pentaerythritol triallyl mono(meth)acrylate, pentaerythritol diallyl di(meth)acrylate and pentaerythritol monoallyl tri(meth)acrylate. The transition metal catalyst may include elements listed in Groups 3 to 12 on the periodic table. For example, the transition metal may comprise a platinum group metal (PGM), such as platinum, ruthenium, rhodium, palladium, osmium or iridium. The transition metal catalyst may also comprise a halogen, such as Cl. The transition metal catalyst is preferably platinum based, for example, $H_2PtCl_6$. Other suitable catalysts are, for example, rhodium-containing compounds.

In one embodiment, the compound of formula (I) is obtained by reaction of (derived from) (meth)acrylate esters of mono- or di-allyl ethers of trimethylol propane with trimethoxy silane or triethoxy silane. The structure of said compound corresponds as follows with respect to formula (I)
A=methyl
B=—$CH_2O(R_2)_m(CH_2)_3SiX_3$, where X is a methoxy or an ethoxy and m=0
C=—$CH_2O(R_2)_m(C$=$OC(R_1))$=$CH_2$, with $R_1$ being methyl or H and m=0
D=—$CH_2O(R_2)_m CH_2C(H)$=$CH_2$ with m=0
and w=1, z=0 or 1, x=1 or 2, y=1 or 2 and w+x+y+z=4.

In another embodiment, the compound of formula (I) is obtained by reaction of (derived from) (meth)acrylate esters of mono- or di-allyl ethers of ethoxylated or propoxylated trimethylol propane with trimethoxy silane or triethoxy silane. The structure of said compound corresponds as follows with respect to formula (I)
A=methyl
B=—$CH_2O(R_2)_m(CH_2)_3SiX_3$, where X is a methoxy or an ethoxy and m=1
C=—$CH_2O(R_2)_m(C$=$OC(R_1))$=$CH_2$, with $R_1$ being methyl or H and m=1
D=—$CH_2O(R_2)_m CH_2C(H)$=$CH_2$ with m=1
$R_2$ being comprised of n units of oxyethylene or of oxypropylene and n being from 1 to 12 and in particular from 1 to 5
and w=1, z=0 or 1, x=1 or 2, y=1 or 2 and w+x+y+z=4.

In another embodiment, the compound of formula (I) is obtained by reaction of (meth)acrylate esters of mono-, di- or tri-allyl ethers of pentaerythritol with trimethoxy silane or triethoxy silane. The structure of said compound corresponds as follows with respect to formula (I)
A=none (w=0)
B=—$CH_2O(R_2)_m(CH_2)_3SiX_3$, where X is a methoxy or an ethoxy and m=0
C=—$CH_2O(R_2)_m(C$=$OC(R_1))$=$CH_2$, with $R_1$ being methyl or H and m=0
D=—$CH_2O(R_2)_m CH_2C(H)$=$CH_2$ with m=0
and w=0, z=0, 1 or 2, x=1, 2 or 3, y=1, 2 or 3 and w+x+y+z=4.

These compositions either curable for coatings or copolymerizable for a copolymer may contain suitable reactive diluents for coatings or comonomers for copolymers, which do copolymerize with said compounds of formula (I) as defined above according to the present invention. An example of suitable comonomers or reactive diluents are monomeric (meth)acrylates. Suitable (meth)acrylates include compounds containing two carbon atoms double bonded to each other and a carbonyl carbon (a carbon atom double-bonded to an oxygen atom). (Meth)acrylates may include, but are not limited to, methyl(meth)acrylate, ethyl (meth)acrylate, propyl(meth)acrylate, n-butyl(meth)acrylate, isobutyl(meth)acrylate, t-butyl(meth)acrylate, pentyl (meth)acrylate, hexyl(meth)acrylate, cyclohexyl(meth) acrylate, benzyl(meth)acrylate, 2-ethylhexyl(meth)acrylate, heptyl(meth)acrylate, n-octyl(meth)acrylate, nonyl(meth) acrylate, decyl(meth)acrylate, undecyl(meth)acrylate, dodecyl(meth)acrylate, tridecyl(meth)acrylate, lauryl(meth)acrylate, stearyl(meth)acrylate, isobornyl(meth)acrylate, norbornyl(meth)acrylate, 4-tertbutylcyclohexyl(meth)acrylate, 3,3,5-trimethylcyclohexyl(meth)acrylate, dimethyl maleate, n-butyl maleate, alkylene glycol di(meth)acrylates, ethylene glycol di(meth)acrylate, 1,3-butylene glycol di(meth)acrylate, 1,4-butylene glycol di(meth)acrylate, propylene glycol(meth)acrylate, 1,6-hexanediol di(meth)acrylate, dipropylene glycol di(meth)acrylate, tripropylene glycol di(meth)acrylate, trimethylolpropane tri(meth)acrylate, cyclopentadienyl(meth)acrylate, carbodiimide(meth)acrylate, t-butylaminoethyl(meth)acrylate, 2-t-butylaminoethyl (meth)acrylate and N,N-dimethylaminoethyl(meth)acrylate.

Is also part of the invention a substrate which is coated with a curable composition or a free radically polymerized polymer or copolymer according to the invention, as resulting from at least one compound of formula (I). More particularly, the said substrate is coated with a hybrid free radical-UV cationic dual cure polymer or copolymer resulting from said compounds. Preferably, said substrate is selected from the group consisting of glass, metal, steel, wood, plastic, composite, cardboard, plaster and concrete.

A reinforced and preferably fiber-reinforced, more particularly glass fiber-reinforced, curable or cured, rubber or elastomer or composite polymer composition comprising said compound, is also part of the present invention.

Finally, the invention relates to uses of the compounds of the invention under formula (I) as defined above, as coupling agents, as adhesion promoters or as monomers in preparing polymers, resins, coatings like varnishes, paints, inks or adhesives and in sealants or composites.

The amounts of the various components in the curable compositions may include, for example, 0.1-30% silane and 30-90% of (meth)acrylate monomers, oligomers or monomer/oligomer mixtures. The composition may also contain other suitable ingredients or additives known to one of ordinary skill in the art, such as photoinitiators, acid initiators, curing accelerators, fillers, reinforcers, catalysts, wetting agents, antioxidants, stabilizers, colorants, pigments, lubricants and the like. Suitable free radical generating photoinitiators may include, but are not limited to, benzophenone, 1-chloromethylnaphthalene, 2-chlorothioxanthone, α,α-diethoxyacetophenone, 2,3-dichloronaphthoquinone, 4,4'-bis(α-chloroacetyl)benzene, α,α,α-trichloroacetophenone, isopropyl benzoin ether, 4'-tert-butyl-α,α,α-trichloroacetophenone, 4,4'-bis(chloromethyl)benzophenone, 4-chloromethyl-4'-carbomethoxybenzophenone, 2-chloromethylbenzimidazole, 2-(α-chlorotolyl)benzoxazole and 4,4'-dimethylbenzophenone. Examples of suitable cationic photoinitiators include, but are not limited to, onium salts, diaryliodonium salts of sulfonic acids, triarylsulfonium salts of sulfonic acids, diaryliodonium salts of boronic acids and triarylsulfonium salts of boronic acids, having non-nucleophilic anions such as hexafluorophosphate, hexafluoroantimonate, tetrafluoroborate and hexafluoroarsenate, tetra(pentafluorophenyl)borate.

Improved properties in peroxide-cured rubber, elastomer and composite compositions may also be obtained, for example, by incorporating fillers and reinforcers, such as carbon black, glass fiber, synthetic fiber and silaceous materials.

In the case of the radiation (e.g., ultraviolet (UV) light, electron beam (EB), or visible light) curable compositions, the compositions may contain, for example, 0.5-10% of silane of formula (II), 0.5-15% of photoinitiator or photoinitiator mixture, and 50-90% of (meth)acrylate monomers, oligomers or monomer/oligomer mixtures.

The various components may be mixed and applied to the substrate surface using any suitable method and techniques known to one of ordinary skill in the art, for example, by roller coating, spray coating, gravure rolling, curtain coating, roll-to-roll lamination, deposition process and the like.

The compositions may be termed curable compositions or free radical curable compositions and may be cured under suitable conditions known to one of ordinary skill in the art. The curable compositions may be UV curable and/or peroxide curable coatings, for example. The compositions may also be useful as resins in hybrid free radical/cationic cure UV curable coatings or 2-part cure coating systems using peroxides and acid (cationic) initiators, for example. Additionally, the compositions may be useful as coupling agents in peroxide cured elastomer and composite resin systems as well as in peroxide cured concrete sealant and bulk cure systems. The compositions may also include reinforced, rubber, elastomer or composite polymer compositions.

The curable compositions may be cured by irradiation with UV light, for example, by exposing the composition to a UV light for a sufficient time to cause curing thereof. Alternatively, the silane agent may be applied first to the substrate followed by a second application of formulated curable composition and curing. The radiation curable composition may include a radiation curable coating, adhesive or sealant composition, for example.

The curable compositions may also be cured by using a peroxide initiator, such as inorganic or organic peroxides. Organic peroxides may include dialkylperoxides, ketalperoxides, aralkylperoxides, peroxide ethers or peroxide esters, for example. Curing may be performed at a suitable temperature selected by one of ordinary skill in the art, for example, a temperature in the range of from about 100 to 200° C. The peroxide curable composition may include a peroxide-curable coating, adhesive, elastomer, rubber, concrete, composite or sealant composition, for example.

The monomer admixture may be applied to a surface of an article and cured to form a coating, adhesive or sealant, for example. The surfaces to which the coating, adhesive or sealant compositions of the invention may be applied include, but are not limited to, glass, metal, wood, steel, plastic, concrete and the like. The monomers in accordance with the invention may be used in the same manner as the prior methacryloxypropyl trimethoxysilane monomer with the advantages of imparting lower odor and having reduced volatility to the radiation curable compositions.

The following examples illustrate several embodiments of the invention.

EXAMPLES

Example 1

Synthesis of Trimethylol Propane Diallyl Ether Monomethacrylate

Trimethylol propane diallyl ether (Perstrorp, TMPDE 90) (655 g), Dow Chemical brand, methacrylic acid (302 g), 4-methoxyphenyl (5 g), methane sulfonic acid (70%, 14 g) and heptane (420 g) were added to a reactor and stirred at room temperature. Air sparge was applied. Then, the mixture was heated to reflux and water generated was removed via azeotrope. After the reaction was complete (no more water formation), the mixture was neutralized with 25% NaOH and washed twice with 25% NaOH, The final product, trimethylol propane diallyl monomethacrylate, was obtained by removing the heptane solvent under reduced pressure. Yield was 808 grams.

The intermediate obtained corresponds to a compound of formula (III) where A is $C_2$ alkyl ($CH_2CH_3$), w=1; C is a methacrylate functional group where m=0, $R_1$ is $CH_3$, y=1; D is an allyl functional group with m=0 and z=2.

Example 2

Synthesis of Trimethylol Propane Diallyl Acrylate

Example 1 was repeated using acrylic acid in the same molar quantity as methacrylic acid.

The intermediate obtained corresponds to a compound of formula (III) where A is $C_2$ alkyl ($CH_2CH_3$), w=1; C is an acrylate functional group where m=0, $R_1$ is H, y=1; D is an allyl functional group with m=0 and z=2.

Example 3

Synthesis of Trimethylol Propane Methacrylate Bis(propyl trimethoxysilane)

The intermediate from Example 1 (49 g, 0.18 moles), trimethoxysilane (44 g, 0.36 moles), 4-methoxyphenol (0.16 g) and a platinum catalyst (4 drops, made by dissolving 2.0 g $H_2PtCl_6$ in 98.0 g isopropanol) were added to a three neck flask and stirred. After 4-methoxyphenol was dissolved, air sparge was applied and the mixture was heated to 85° C. The addition reaction took place with the observation of an exotherm. The reaction was followed by FTIR with the disappearance of Si—H stretch at 2200 $cm^{-1}$. The reaction was completed in 8 hrs.

The reaction product obtained corresponds to Formula (I) where A is $C_2$ alkyl ($CH_2CH_3$), w=1; B is a silane functional group with formula —$CH_2O(R_2)_m(CH_2)_3SiX_3$ where m=0, X=C alkoxy (methoxy) and x=2; C is a methacrylate functional group where m=0, y=1, $R_1$ is $CH_3$ and z=0.

While the invention has been described in great detail, various alternatives and improvements should become apparent to those skilled in this art without departing from the spirit and scope of the invention as set forth in the claims.

The invention claimed is:

1. A compound or a mixture of compounds of formula (I):

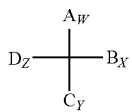

(I)

wherein
- A is a $C_1$-$C_{12}$ organic moiety,
- B is a silane functional group with formula —$CH_2O(R_2)_m(CH_2)_3SiX_3$ where X=a halogen, a $C_1$-$C_6$ alkyl, a $C_1$-$C_6$ alkoxy or an aromatic radical,
- C is a (meth)acrylate functional group with formula $CH_2O(R_2)_m(C=O)C(R_1)=CH_2$ where $R_1$ is H or $CH_3$,
- D is an allyl functional group with formula —$CH_2O(R_2)_mCH_2C(H)=CH_2$, and w=0 or 1, x=2 or 3, y=1 or 2, and z=0, 1 or 2, and w+x+y+z=4, where $R_2$ for each functional group is the same or different and is an oxyalkylene or polyoxyalkylene unit comprised of n repeating units of oxyalkylene, a caprolactone or polycaprolactone unit comprised of n repeating units of formula —[C(=O) $(CH_2)_5$O]— or a lactide or polylactide unit, comprised of n repeating units of formula —[C(=O)CH($CH_3$)O]—, n is an integer with a value from 1 to 12 and m is 0 or 1.

2. A compound according to claim 1, wherein z=0 or 1, w=1, A is a $C_1$ or $C_2$ alkyl group, $R_1$ is $CH_3$ or H, m=0 and X is methoxy or ethoxy.

3. A compound according to claim 1, wherein z=0 or 1, w=1, A is a $C_1$ or $C_2$ alkyl group, $R_1$ is $CH_3$ or H, m=1, n=1 to 5, where $R_2$ is an oxyalkylene or polyoxyalkylene unit and X is methoxy or ethoxy.

4. A compound according to claim 1, wherein z=0 or 1, w=0, $R_1$ is $CH_3$ or H, m=0 and X is methoxy or ethoxy.

5. A compound according to claim 1, wherein z=0 or 1, w=0, $R_1$ is $CH_3$ or H, m=1, n=1 to 5, $R_2$ is an oxyalkylene or polyoxyalkylene unit and X is methoxy or ethoxy.

6. A compound according to claim 1, wherein $R_2$ is an oxyalkylene or polyoxyalkylene unit of formula —[$CH_2CH_2O$]$_n$— or —[$CH_2CH(CH_3)O$]$_n$— where n is an integer with a value from 1 to 12.

7. A compound according to claim 1, wherein the compound is derived from the reaction of (meth)acrylate esters of mono- or di-allyl ethers of trimethylol propane with trimethoxy silane or triethoxy silane.

8. A compound according to claim 1, wherein the compound is derived from the reaction of (meth)acrylate esters of mono- or di-allyl ethers of ethoxylated or propoxylated trimethylol propane with trimethoxy silane or triethoxy silane.

9. A compound according to claim 1, wherein the compound is derived from the reaction of (meth)acrylate esters of mono-, di- or tri-allyl ethers of pentaerythritol with trimethoxy silane or triethoxy silane.

10. A compound according to claim 1, wherein the compound is obtained by the reaction of (meth)acrylate esters of mono-, di- or tri-allyl ethers of ethoxylated or propoxylated pentaerythritol with trimethoxy silane or triethoxy silane.

11. A curable composition, wherein the curable composition comprises at least one compound as defined according to claim 1.

12. A curable composition according to claim 11, wherein said curable composition is or comprises, a peroxide-curable or a radiation-curable composition which is a free radical-curable, a cationic-curable or a dual-curable free radical and cationic hybrid curable composition.

13. A curable composition according to claim 12, wherein said curable composition is a peroxide-curable coating, adhesive, elastomer, rubber, concrete, composite or sealant composition.

14. A curable composition according to claim 12, wherein said curable composition is a radiation curable coating, adhesive or sealant composition.

15. A substrate coated with a curable composition as defined according to claim 11.

16. A substrate according to claim 15, wherein said substrate is selected from the group consisting of glass, metal, steel, wood, plastic, composite, cardboard, plaster and concrete.

17. A method of making a compound according to claim 1, comprising reacting a silane compound of formula (II)

$$H—Si(X)_3 \qquad (II)$$

on at least one allyl functionality of the precursor compound of formula (II):

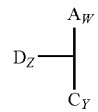

where:
- A is a $C_1$-$C_{12}$ organic moiety,
- C is a (meth)acrylate functional group with formula —$CH_2O(R_2)_m(C=O)C(R_1)=CH_2$ where $R_1$ is H or $CH_3$,
- D is an allyl functional group with formula —$CH_2O(R_2)_mCH_2C(H)=CH_2$, and w=0 or 1, y=1, 2 or 3 and z=1, 2 or 3 and w+y+z=4, where $R_2$ for each functional group is the same or different and is an oxyalkylene or polyoxyalkylene unit comprised of n repeating units of oxyalkylene such as oxyethylene [$CH_2CH_2O$] or oxypropylene [$CH_2CH(CH_3)O$], a caprolactone or polycaprolactone unit, comprised of n repeating units of formula —[C(=O) $(CH_2)_5$O]— or a lactide or polylactide unit, comprised of n repeating units of formula —[C(=O)CH($CH_3$)O]—, n being an integer with a value from 1 to 12 and m is 0 or 1 in the presence of a transition metal catalyst.

* * * * *